(12) United States Patent
Oskarsson et al.

(10) Patent No.: US 10,597,492 B2
(45) Date of Patent: Mar. 24, 2020

(54) DIALKYL-POLYALKYLAMINE COMPOSITIONS, PROCESS FOR THEIR PREPARATION AND THEIR USE

(71) Applicant: NOURYON CHEMICALS INTERNATIONAL B.V., Arnhem (NL)

(72) Inventors: Hans Oskarsson, Stenungsund (SE); Lynnette Susan Bowen, Merseyside (GB); John André Janiak, Göteborg (SE); Elliot Isaac Band, Pleasantville, NY (US); Kristan Alexander Rus, Amersfoort (NL)

(73) Assignee: NOURYON CHEMICALS INTERNATIONAL B.V., Arnhem (NL)

(*) Notice: Subject to any disclaimer, the term of this patent is extended or adjusted under 35 U.S.C. 154(b) by 0 days.

(21) Appl. No.: 16/080,079

(22) PCT Filed: Feb. 24, 2017

(86) PCT No.: PCT/EP2017/054281
§ 371 (c)(1),
(2) Date: Aug. 27, 2018

(87) PCT Pub. No.: WO2017/148808
PCT Pub. Date: Sep. 8, 2017

(65) Prior Publication Data
US 2019/0062500 A1    Feb. 28, 2019

Related U.S. Application Data

(60) Provisional application No. 62/300,992, filed on Feb. 29, 2016.

(30) Foreign Application Priority Data

Mar. 18, 2016 (EP) .................................. 16161213

(51) Int. Cl.
| | | |
|---|---|---|
| C08G 73/02 | (2006.01) | |
| C10M 133/06 | (2006.01) | |
| C09K 8/54 | (2006.01) | |
| C09K 8/588 | (2006.01) | |
| C10M 149/14 | (2006.01) | |
| C09K 8/26 | (2006.01) | |

(52) U.S. Cl.
CPC ............ C08G 73/0213 (2013.01); C09K 8/26 (2013.01); C09K 8/54 (2013.01); C09K 8/588 (2013.01); C10M 133/06 (2013.01); C10M 149/14 (2013.01); C09K 2208/32 (2013.01); C10M 2215/04 (2013.01); C10M 2217/046 (2013.01);
(Continued)

(58) Field of Classification Search
CPC ............ C08G 73/0213; C10M 133/06; C10M 2217/046; C10M 2215/04; C10N 2240/401; C10N 2230/12; C10N 2250/021; C10N 2220/021; C10N 2220/022; C10N 2220/03; C10N 2230/24; C10N 2230/52
See application file for complete search history.

(56) References Cited

U.S. PATENT DOCUMENTS

| | | |
|---|---|---|
| 3,259,512 A | 7/1966 | Dickson et al. |
| 3,418,374 A | 12/1968 | Miller, Jr. et al. |
| | (Continued) | |

FOREIGN PATENT DOCUMENTS

| | | |
|---|---|---|
| CN | 1995009 A | 7/2007 |
| CN | 103936603 A | 7/2014 |
| | (Continued) | |

OTHER PUBLICATIONS

XP55365027, Pieri et al., "First Evidence for the Use of Polyamines as Nucleophiles in a Regioselective Palladium-Catalyzed Allylic Amination Reaction", Tetrahedron vol. 70, No. 51, Oct. 12, 2014, pp. 9718-9725.
(Continued)

*Primary Examiner* — Shane Fang
(74) *Attorney, Agent, or Firm* — Lorenz & Kopf, LLP

(57) ABSTRACT

The application relates to compositions comprising di-fatty-alkyl or -alkenyl polyalkylamines of the general formula (I) or (II), to a process for their preparation which involves a cyanoethylation step and a hydrogenation step, and their use as demulsifiers for oil-in-water emulsions, corrosion inhibitor, fuel additive, anti-scaling agent, asphalt additive, enhanced oil recovery agent for oil-wells, cutting-oil additive, and anti-static agent. The product show good performance combined with a favourable viscosity profile.

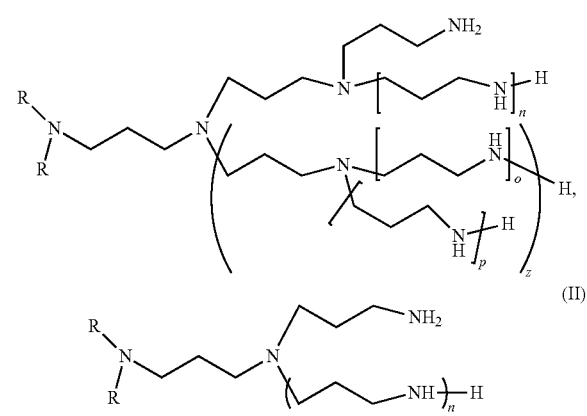

20 Claims, No Drawings

(52) U.S. Cl.
CPC .. *C10N 2220/021* (2013.01); *C10N 2220/022* (2013.01); *C10N 2220/03* (2013.01); *C10N 2230/12* (2013.01); *C10N 2230/24* (2013.01); *C10N 2230/52* (2013.01); *C10N 2240/401* (2013.01); *C10N 2250/021* (2013.01)

(56) References Cited

U.S. PATENT DOCUMENTS

| | | | |
|---|---|---|---|
| 3,518,101 | A | 6/1970 | Gzemski et al. |
| 3,615,797 | A | 10/1971 | Ohtsuka et al. |
| 3,642,663 | A | 2/1972 | Greer |
| 3,738,852 | A | 6/1973 | Doi et al. |
| 4,967,008 | A | 10/1990 | Friedli et al. |
| 5,073,297 | A | 12/1991 | Schilling |
| 5,254,737 | A | 10/1993 | Zimmerman |
| 6,494,944 | B1 | 12/2002 | Wates et al. |
| 6,667,382 | B1 | 12/2003 | Isobe et al. |
| 7,226,501 | B2 | 6/2007 | Thorstensson et al. |
| 7,608,142 | B2 | 10/2009 | Thorstensson et al. |
| 2003/0049310 | A1 | 3/2003 | Gao |
| 2013/0296210 | A1 | 11/2013 | Hansch et al. |
| 2018/0223218 | A1* | 8/2018 | Doyen ................. C10M 133/06 |
| 2018/0371356 | A1* | 12/2018 | Roussel ............. C10M 169/044 |

FOREIGN PATENT DOCUMENTS

| | | |
|---|---|---|
| FR | 2 539 754 A1 | 7/1984 |
| FR | 2 834 715 A1 | 7/2003 |
| GB | 2 015 520 A | 9/1979 |
| RU | 2 556 204 C2 | 7/2015 |
| WO | 00/39241 | 7/2000 |
| WO | 2006/076929 A1 | 7/2006 |
| WO | 2011/000895 A1 | 1/2011 |
| WO | 2011/0105372 A1 | 5/2011 |
| WO | 2013/017886 A1 | 2/2013 |

OTHER PUBLICATIONS

XP002195935, Williams et al., "Motuporamines, Anti-Invasion and Anti-Angiogenic Alkaloids From the Marine Sponge *Xestospongia exigua*(Kirkpatrick): Isolation, Structure Elucidation, Analogue Synthesis, and Confromational Analysis", The Journal of Organic Chemistry, vol. 67, No. 1, 2002, pp. 245-258.

European Search Report issued in the counterpart European Application No. 16161213.0 dated Sep. 13, 2016.

Notification of Transmittal of the International Search Report and the Written Opinion of the International Searching Authority, or the Declaration from the International Bureau of WIPO for International Application No. PCT/EP2017/054281 dated May 4, 2017.

* cited by examiner

DIALKYL-POLYALKYLAMINE COMPOSITIONS, PROCESS FOR THEIR PREPARATION AND THEIR USE

This application is a national stage filing under 35 U.S.C. § 371 of PCT/EP2017/054281, filed Feb. 24, 2017, which claims priority to U.S. Patent Application No. 62/300,992, filed Feb. 29, 2016, and European Patent Application No. 16161213.0, filed Mar. 18, 2016, the contents of which are each incorporated herein by reference in their entireties.

FIELD OF THE INVENTION

The present invention relates to compositions of di-fatty-alkyl(ene) polyalkylamines whereof the polyalkylamine-moiety shows a specific level of branching, a process to make such compositions, and their use in various applications.

BACKGROUND OF THE INVENTION

Alkyl(ene) polyalkylamines are well known and are used, inter alia, in asphalt applications.

WO 2006/076929 discloses, as intermediates in the synthesis of fully tertiary mono-fatty-alkyl polyalkylamines, a fully linear product with one fatty alkyl moiety. Although the reaction pathway is mentioned, the reaction conditions are not clear and the products, that have only one fatty alkyl moiety, seem to be pure. Salts of the fully tertiary mono-fatty-alkyl triamines are mentioned to be suitable for use in aqueous slow-setting bitumen-aggregate mixtures.

U.S. Pat. No. 4,967,008 relates to mono-fatty-alkyl polyalkylamines with primary, tertiary and optionally secondary amine moieties. An exemplified product is linear N-tallow-N-methyl dipropylene triamine. Because the intermediate in the process of U.S. Pat. No. 4,967,008 is methylated before the second cyanoethylation step, there is no branching in the products.

From CAS registration number 1623405-26-4, a linear di-fatty-alkyl tetramine with CAS-name "Amines, N'-{3-[(3-aminopropyl)amino]propyl}-N,N-di-C16-18 alkyltrimethylenedi-" is known.

US2003/049310 discloses a large amount of cationic lipids and the use thereof in liposomes to introduce functional bioactive agents to cultures cells. Mixtures of polyamines as claimed are not disclosed or suggested.

For lubricating oils a variety of amines have been evaluated in the past. Particular for 2-stroke marine engines it is known that due to changes in emission regulations, as well because of the different fuels used, there is a need for an improved amine formulation for use in lubricating oils, particularly for use in lubrication oils used in engines that burn sulfur-containing oils, particularly for lubrication of 2-stroke diesel marine engines.

Surprisingly it was found that compositions of di-fatty-alkyl(ene) tetramines with a specific amount of linear and branched molecules show excellent properties when used in lubrication oils and other applications where polyalkylamines are known to be used, such as in demulsifiers for oil-in-water emulsions, generic use as a corrosion inhibitor, fuel additive, anti-scaling agent, asphalt additive, enhanced oil recovery from oil-wells, cutting-oil additive, and anti-static agent. Furthermore, it was found that the claimed processes to make the di-fatty-alkyl(ene) tetramines is very economic in producing the desired compositions.

Accordingly, the invention relates to such di-fatty-alkyl (ene) polyalkylamine compositions which comprise mixtures of one or more polyalkylamines selected from products of the formulae (I) and (II)

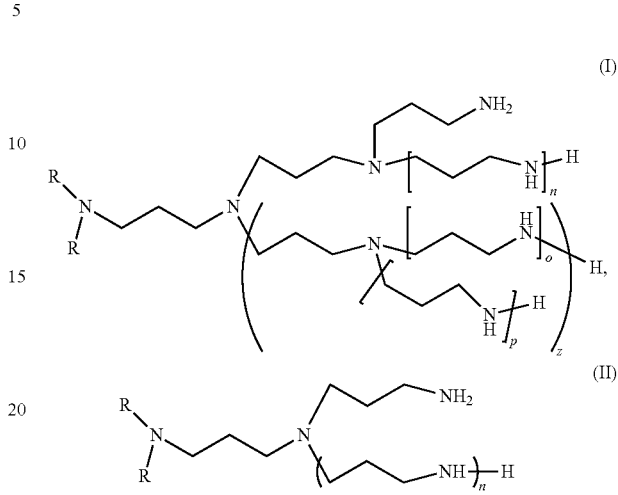

wherein each R is, independent of the other R, a fatty-alkyl or fatty-alkylene moiety, herein defined as to have 8-22 carbon atoms, which is linear or branched, n and z are independent of each other either 0, 1, 2, or 3, and when z>0 then o and p are independent of each other either 0, 1, 2, or 3, or derivatives thereof, whereby said mixture comprises at least 3% by weight of branched products whereof at least one of n and z>=1. and whereby said mixture comprises at least 5% by weight of products with a pure linear structure. Such mixtures with both linear and branched products were found to have a desirable viscosity profile.

In an embodiment the amount of products with linear structure in the mixture is 6, 7.5, 10, or 14% by weight, or more, based on the weight of all polyalkylamines. In an embodiment the linear product in the mixture is of formula (I) with n and z being 0. In an embodiment the linear product in the mixture is of formula (II) with n is 0.

In an embodiment the mixtures comprise at least 4% by weight (%w/w), suitably at least 5% w/w, suitably at least 6% w/w, suitably more than 7% w/w, suitably more than 7.5% w/w, suitably more than 10% w/w, suitably more than 20% w/w, of branched compounds whereof, for the products of formula (I), at least one of n and z>=1, based on the weight of all polyalkylamines. For the products of formula (II) this means that for the branched products n must be >=1.

It is noted that whenever n, o, p, or z is 0 then the hydrogen is covalently bound to the nitrogen. For economic reasons each of n, o, p, and z, independently and when not 0, are 1 or 2, preferably 1.

Although the two R groups can be different, they are, in one embodiment, the same, since such materials are more economically produced. Irrespective of whether they are the same or not, one or both of the R groups, independently, are typically derived from chemical feedstock or from a natural source, such as from natural oils and fats. Particularly if a natural source is used, it means that each R group may have a certain distribution in the carbon chain length. Suitably R is derived from animal and vegetal oils and fats, such as tallow, coco and palm oil. Since making the di-fatty-alkyl (ene) polyalkylamines in accordance with the invention comprises a hydrogenation step, it may be beneficial to use hydrogenated R groups before the products of the invention are prepared using a process as claimed. However, for certain feedstocks, even after hydrogenization, an appreciable amount of unsaturated bonds may remain. Suitably a fully hydrogenated tallow group is used as the R group, and the corresponding mixture of di-fatty-alkyl polyalkyl amines are formed. Alternatively, the raw material for the R group is unsaturated whereby the unsaturated R group may be wholly or partially hydrogenated during the process to make the claimed di-fatty-alkyl(ene) polyalkylene amines being a mixture of di-fatty-alkyl polyalkylene amines and di-fatty-alkylene polyalkylene amines. Also products with one fully saturated R group and one unsaturated R group are products of the invention.

Therefore, as used herein, "di-fatty-alkyl(ene) polyalkylamines" refers to di-fatty-alkyl polyalkylamines, di-fatty-alkylene polyalkylamines, fatty-alkyl fatty-alkylene polyalkylamines, and mixtures thereof.

The term "consisting" wherever used herein also embraces "consisting substantially", but may optionally be limited to its strict meaning of "consisting entirely".

Throughout the description and claims of this specification, the words "comprise" and "contain" and variations of the words, for example "comprising" and "comprises", mean "including but not limited to", and do not exclude other moieties, additives, components, integers or steps. Moreover the singular encompasses the plural unless the context otherwise requires: in particular, where the indefinite article is used, the specification is to be understood as contemplating plurality as well as singularity, unless the context requires otherwise.

Where upper and lower limits are quoted for a property, for example for the concentration of a component, then a range of values defined by a combination of any of the upper limits with any of the lower limits may also be implied.

It should be appreciated that the various aspects and embodiments of the detailed description as disclosed herein are illustrative of the specific ways to make and use the invention and do not limit the scope of invention when taken into consideration with the claims and the detailed description. It will also be appreciated that features from different aspects and embodiments of the invention may be combined with features from different aspects and embodiments of the invention.

Derivatives of the di-fatty-alkyl(ene) polyalkylamines compositions of the invention include products wherein one or more of the NH moieties of the dialkyl polyalkylamines of the invention are methylated, alkoxylated, or both. Such products were found to have desirable solubility of the dialkyl polyalkylamines, particularly in lubricating oils. Alkoxylated derivatives are suitably butoxylated, propoxylated and/or ethoxylated. If two or more different alkoxylation agents are used then can be used in any sequence, e.g. EO-PO-EO, and the various alkoxy units can be of blocky nature and/or be present in a random fashion. Suitably a primary —$NH_2$ group is alkoxylated with one or more alkylene oxides in a conventional way to form a —NH-AO-H group, wherein AO stands for one or more alkyleneoxy units. The resulting —NH-AO-H group can be further alkoxylated to form —N (AO-H)$_2$ groups. Especially when large amounts of alkylene oxide (i.e. when more than 8 AO molecules per polyalkylamine molecule) are used, typically also one or more of the secondary amine functions, if present, are alkoxylated. In an embodiment all primary and secondary amine functions of the di alkyl polyamine are alkoxylated. In another embodiment the di-fatty-alkyl(ene) polyalkylamines are derivatized by methylating one or more of the N—H functions in a conventional way, for example by reaction with formic acid and formaldehyde. In another embodiment one or more of the O—H functions of an alkoxylated di-fatty-alkyl(ene) polyalkylamines is methylated in a conventional way.

Although the inventors do not wish to be bound by the following theory, it is believed that the beneficial properties of the dialkyl polyalkylamines compositions as claimed, when compared to the fully branched or fully linear products, lie in the special interaction of the amines in the composition. More specifically, the mixture of linear and branched products are believed to be the components for achieving the desired combination of rheological and anti-corrosion properties of the fluids in which the composition is used.

In view of this theory, it can be preferred to have products with a multitude of differently branched molecules. In that case, compositions comprising mixtures of polyalkylamines of the formula (I) are preferred. However, since compositions comprising mixtures of polyalkylamines of the formula (II) can be more economical to make, under specific circumstances compositions comprising mixtures of polyalkylamines of the formula (II) may be preferred. If suitable, compositions comprising mixtures of dialkyl(ene) polyalkylamines of the formulae (I) and (II) are used.

In one embodiment the invention relates to the use of a composition comprising both the branched products in combination with a linear product according to formula 1 wherein n and z are 0, which composition was found to also show the desired rheology and properties.

The claimed compositions are suitably used as demulsifier for oil-in-water emulsions, corrosion inhibition, fuel additive, anti-scaling agent, asphalt additive, enhanced oil recovery agent from oil-wells, cutting-oil additive, anti-static agent, and additive in lubricating oils, particularly in lubricating oils for machines with varying amounts of acidic, specifically sulfuric acid, contaminants. One particular interesting field of use is in 2-stroke marine diesel engines which are typically operated with different fuels, each with different sulfur content, depending on availability, price, and environmental regulations.

The dialkyl(ene) polyalkylamines mixtures as claimed can be produced using conventional process steps that are conducted in such order and way that the claimed mixtures are obtained. A suitable way to produce them is described in the experimental section below starting from a diamine and involving two or more cycles, for economic reasons preferably two, with each a cyanoethylation step and a hydrogenation step, hereinafter the two-cycle process. However, an alternative process wherein one equivalent of a di-alkyl-diamine is reacted in one step with two or more equivalents of acrylonitrile followed by hydrogenation, and optional further cycles involving a cyanoethylation and hydrogenation step, can be beneficial since it requires less reaction steps.

For increased branching in the two-cycle process, an acidic catalyst is used, such as HCl or acetic acid. Also increasing the reaction temperature during cyanoethylation will result in increased branching in this process. In an embodiment of a multicycle process, the temperature of a later cyanoethylation step is higher than the temperature in an earlier cyanoethylation step, to get a product with the desired branching. In an embodiment more than 1 mole of acrylonitrile is used per mole of the starting polyamine, which was also found to increase the branching of the resulting product to the desired level.

The temperature in each cyanoethylation step is suitably selected in the range from 70 to 125° C. In an embodiment the reaction is conducted, for economic reasons, at a temperature up to 80, 85, 90, 95, or 100° C.

For maintaining a homogeneous reaction mixture a solvent is suitably used. Suitable solvents include $C_{1-4}$ alcohols and $C_{2-4}$ diols. Ethanol may be a solvent of choice for ease of handling. Surprisingly the $C_{1-4}$ alcohols and $C_{2-4}$ diols were found not to be mere solvents. They turned out to also have co-catalytic activity in the cyanoethylation step.

The amount of solvent to be used can vary over a wide range. For economic purposes, the amount is typically kept at a minimum. The amount of solvent, particularly in a cyanoethylation step, is suitably less than 50, 40, 30, or 25% by weight of the liquid reaction mixture. The amount of solvent, particularly in a cyanoethylation step, is suitably more than 0.1, 0.5, 1, 5, or 10% by weight of the liquid reaction mixture.

The di-fatty-alkyl(ene) polyalkylamines compositions of the invention were found to be particularly suitable as a corrosion inhibitor, particularly in cutting-oils and lubricating oils. However, they are also suitably used as a demulsifier for oil-in-water emulsions, a fuel additive, an anti-scaling agent, an asphalt additive, an enhanced oil recovery agent for oil-wells, and as an anti-static agent.

EXPERIMENTAL

Duomeen® 2HT is available from AkzoNobel.

Other chemicals were sourced from SigmaAldrich, unless indicated differently.

Example 1

A fully branched product with 4 amine functions was prepared using a 1 L glass reactor with turbine stirrer to which chemicals can be dosed using a Prominent Gamma/L membrane pump and which was thermostatted using a Lauda K6KP heating bath.

Raw Materials

| Chemical | Supplier | Intake (g) | Molw. (g/mol) | Intake (mol) |
| --- | --- | --- | --- | --- |
| Duomeen 2HT | AkzoNobel | 342.0 | 566 | 0.604 |
| Hydrochloric acid (36%) | J T Baker | 3.06 | 36.5 | 0.014 |
| Water | Tap | 1.12 | 18.0 | 0.062 |
| Isopropanol | J T Baker | 34.2 | 60.1 | 0.569 |
| Sodium carbonate | Acros | As needed, see text | | |
| Acrylonitrile | Acros | 81.5 | 53.1 | 1.299 |
| Raney Cobalt | CatAlloy | As needed, see text | | |
| Ammonia | Air products | As needed, see text | | |

Procedure & Results

The cyano-ethylation step is performed by charging the reactor with Duomeen 2HT, isopropanol (co-catalyst and solvent for the dicyano-product that is formed), water, and HCl, and subsequent dosing, in approximately three hours, of the acrylonitrile. Reaction pathway:

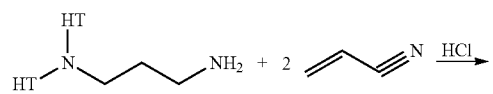

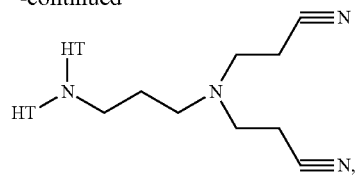

wherein HT stands for hydrogenated tallow.

After a conversion of 80% the reaction rate was so slow that the reaction was stopped. Vacuum was applied to the reactor the temperature was increased to 110° C. to remove the acrylonitrile, water & IPA. The product was washed and neutralized in two steps with 4% $Na_2CO_3$ solution to remove all HCl, and subsequently hydrogenated using the same equipment. Reaction pathway:

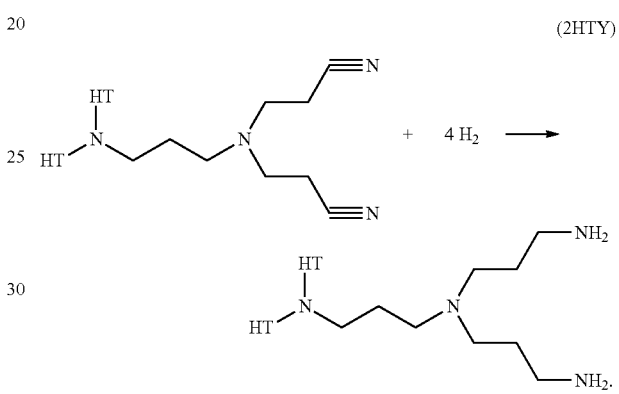

Thereto the stirred reactor containing the dicyano-product was charged with a conventional Raney Cobalt catalyst, such as A-7000 ex Johnson Matthey or Acticat®1100 ex CatAlloy, and subsequently heated to 130° C. while sparging with nitrogen, to remove traces of acrylonitrile and water. Then the reactor was charged with ammonia (13-14 barg) while kept at a temperature of 105° C. Then the reactor was heated to 150° C., and hydrogen was added to maintain a pressure of 49 barg. After completion of the reaction, the temperature was lowered to 80° C. and remaining hydrogen and ammonia were flushed out using nitrogen.

The resulting composition was analyzed using GC-MS and found to contain >70% of the product 2HTY of formula (II) with n=1, as well as more than 14% w/w of the linear product $(HT)_2N-(CH_2)_3-NH-(CH_2)_3-NH_2$, a little starting product $(HT)_2N-(CH_2)_3-NH_2$, and some unidentified further alkylamines.

Example 2A and 2B

A mixture of linear and branched product (Tetrameen 2HTb) was prepared by the two cycle procedure wherein the cyano-ethylation and the hydrogenation steps above were repeated. The 0.6 mole of the Duomeen 2HT was combined with 0.65 mole of acrylonitrile and reacted in the first cyano-ethylation step. After hydrogenation, the triamine was combined with another 0.65 mole of acrylonitrile and reacted. At the end of each cyano-ethylation step, NMR was used to analyze the reaction mixture and to determine if one mole of acrylonitrile had reacted per mole of starting material. If the reaction was found to be too low, some additional acrylonitrile was dosed and after 1 hour the analysis was repeated. This cycle was repeated till the desired reaction was obtained. The final product was analyzed using GC-MS applying the following conditions

| | |
|---|---|
| Gas chromatograph | TRACE ULTRA GC Interscience |
| MS system | ISQ GC-MS |
| Column | Fused silica WCOT, 20 m × 0.32 mm ID |
| stationary phase | Sil 5 CB, 100% polydimethyl-siloxane, cross-linked |
| film thickness | 0.12 μm |
| Carrier gas | Helium |
| flow | 2 ml/min. |
| Temperatures | |
| injector | 275° C. |
| column | initial: 200° C. during 1 min |
| | rate: 20° C./min |
| | final: 310° C. during 15 min |
| Injection volume | 1 μl, approx. 250 mg sample in 10 ml cyclohexane |

In the examples no additional acrylonitrile had to be added after the first cyanoacrylation step which was conducted at a temperature of 85° C. and 75° C., for examples 2a and 2b respectively. In the second cyanoacrylation step the temperature was 85 and 80° C., for examples 2a and 2b respectively. In example 2a an additional amount of 0.025 mole of acrylonitrile was needed to complete the second cyanoacrylation step while in example 2b an additional amount of 0.12 mole of acrylonitrile was added before the addition of 0.60 mole of acrylonitrile was achieved. The highest amount of branching was observed in the sample 2a that was highest in temperature.

It was confirmed that the off-white products, which were pasty/viscous liquids at room temperature, contained more than 13.8% w/w of branched product of formula (I) with one or more of n and z>=1, and also contained more than 14% w/w of the linear product with n=z=0.

Examples 3-5

To a commercial lubricant (Talusia HR70, which is overbased and comprises $CaCO_3$, from Total LubeMarine), 5 wt % of the 2HTb of example 2a, 2HTY, or a 50/50 blend of 2HTY and 2HTb was added and thoroughly blended, followed by neutralization of 50 BN points of the lubricant composition with 95% sulfuric acid, in order to simulate the phenomenon of neutralization of the composition to be closer to real conditions of use of the lubricating composition in a marine engine.

In this process the amines together with the overbased detergents neutralizes the sulfuric acid. The generated sulfate ions become the counterions of the positively charged ammonium groups and/or react with the calcium of the $CaCO_3$ to form gypsum, $CaSO_4$.

Measurements of the viscosity (Pa·s) at 40° C. of the three acidized blends of lubricant and alkylpolyamines, as prepared above, were performed by measuring the viscosity at a shear rate of 0.05 s−1 as displayed in the tables. All measurements were performed at 40° C. on an AR-G2 rheometer from TA-instruments.

TABLE 1

| Product | Viscosity Pa · s |
|---|---|
| 2HTb | 0.3639 |
| 2HTY | 0.3838 |
| 50/50 of 2HTb/2HTY | 0.3561 |

All of these samples show an acceptable viscosity.

Comparative Examples A-C

Acidized blends of a commercial mono-oleyl tripropylenetetramine of AkzoNobel (Tetrameen OV) and a commercial mono-tallow tripropylenetetramine of AkzoNobel (Tetrameen T) in lubricant, prepared as described for Examples 3-5, were analyzed for its viscosity and compared with the viscosity of the 2HTb blend and lubricant only.

TABLE 2

| Product | Viscosity Pa · s |
|---|---|
| Tetrameen OV | 0.8061 |
| Tetrameen T | 2.705 |
| 2HTb | 0.3639 |
| Base oil | 0.2695 |

The results show that Tetrameen OV and Tetrameen T resulted in an unacceptable viscosity of the acidized blend.

Comparative Examples D-F

Acidized blends of a commercial di-hydrogenated tallow dipropylenetriamine of AkzoNobel (Triameen® 2HT) and a commercial di-hydrogenated tallow propylenediamine of AkzoNobel (Duomeen® 2HT) in lubricant, prepared as described for Examples 3-5, whereby the amount of the triamine was increased to 6.2% w/w and the amount of Duomeen was increased to 8% w/w to achieve the same total base number, were analyzed for its viscosity and compared with the viscosity of the blends of comparative example A-C. The viscosity (Pa·s) at a shear rate of 0.05 s−1 was found to be between the viscosity for Tetrameen OV and Tetrameen T, so again showing an undesired high viscosity.

Mental Example 6

In this example the compounds of Examples 1, 2a and 2b are used as demulsifiers for oil-in-water emulsions, corrosion inhibitor, fuel additive, anti-scaling agent, asphalt additive, enhanced oil recovery agent for oil-wells, cutting-oil additive, and anti-static agent. They show the typical performance, but also a viscosity profile which is surprising for di-fatty-alkyl(ene) polyalkylamines with this molecular weight.

The invention claimed is:
1. Di-fatty-alkyl(ene) polyalkylamine composition which comprises a mixture of polyalkylamines selected from products with formulae (I) and (II),

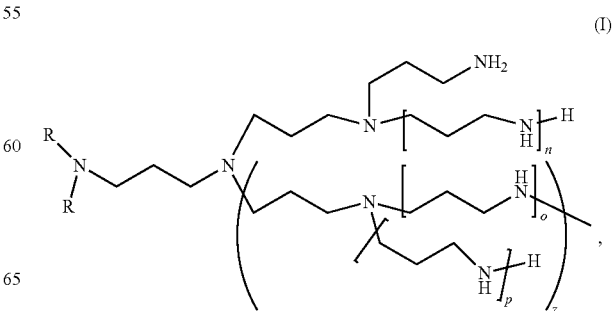

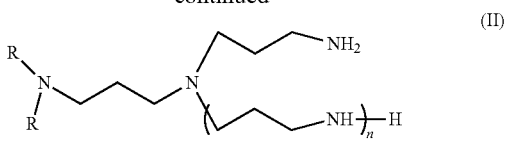

(II)

wherein each R is, independent of the other R, an alkyl or alkylene moiety with 8-22 carbon atoms, n and z are independent of each other either 0, 1, 2, or 3, and when z>0 then o and p are independent of each other either 0, 1, 2, or 3, or derivatives thereof, whereby said mixture comprises a) a total of at least 3% by weight of branched compounds of formula (I) with at least one of n and z>=1 and products of formula (II) with n>=1, and b) a total of at least 5% by weight of products of formula (I) with n and z=0, and compounds of formula (II) with n=0.

2. Polyalkylamines composition according to claim 1 comprising a total of at least 4% w/w of branched compounds of formula (I) with at least one of n and z<>0 and compounds of formula (II) with n<>0.

3. Polyalkylamines composition according to claim 1 comprising at least 5% by weight of products of formulae (I) and (II) with a linear structure with n is 0 in formulae (I) and (II) and z is 0 in formula (I).

4. Polyalkylamines composition of claim 1 comprising derivatives of di-fatty-alkyl(ene) polyalkylamines, wherein the derivatives are alkoxylates which are optionally methylated.

5. Polyalkylamines composition of claim 1 comprising derivatives of di-fatty-alkyl(ene) polyalkylamines, wherein the derivatives are methylated.

6. A process for making the polyalkylamines compositions of claim 1 wherein a di-fatty-alkyl(ene) alkyldiamine is reacted in two or more cycles whereby each cycle comprises a cyanoethylation step and a subsequent hydrogenation step.

7. A process of claim 6 wherein an acidic catalyst is used during the cyanoethylation steps.

8. A process of claim 6 wherein the reaction temperature during a later cyanoethylation step is higher than the temperature in an earlier cyanoethylation step.

9. A process of claim 6 wherein more than 1 mole of acrylonitrile is used per mole of the starting polyamine.

10. A process for making the polyalkylamines compositions of claim 1 wherein a di-fatty-alkyl(ene) alkyldiamine is subjected to a cyanoethylation step and a subsequent hydrogenation step, whereby in the cyanoethylation step at least 2 mole of acrylonitrile is used per mole of di-fatty-alkyl(ene) alkyldiamine and an acidic catalyst is used.

11. A process of claim 10 wherein the product is subjected to one or more further cycles comprising a cyanoethylation and subsequent hydrogenation step.

12. A process according to claim 6 wherein one or more solvents selected from $C_{1-4}$ alcohol and $C_{2-4}$ dials is present in the cyanoethylation step.

13. A process of claim 12 wherein the amount of solvent is from 0.1 to 50% by weight of the liquid reaction mixture.

14. A process to make the derivatives of claim 4 wherein a di-fatty-alkyl(ene) alkyldiamine is reacted in two or more cycles whereby each cycle comprises a cyanoethylation step and a subsequent hydrogenation step, with an additional step wherein the di-fatty-alkyl(ene) polyalkylamines are methylated, alkoxylated, or both.

15. A method comprising adding the di-fatty-alkyl(ene) polyalkylamine composition of claim 1 to an oil-in-water emulsion.

16. A method comprising adding the di-fatty-alkyl(ene) polyalkylamine composition of claim 1 to a formulation, wherein the formulation is suitable for use as a corrosion inhibitor, a fuel additive, an anti-scaling agent, an asphalt additive, an enhanced oil recovery agent for oil-wells, a cutting-oil additive, and an anti-static agent.

17. Polyalkylamines composition according to claim 1 comprising a total of at least 5% w/w of branched compounds of formula (I) with at least one of n and z<>0 and compounds of formula (II) with n<>0.

18. Polyalkylamines composition according to claim 1 comprising a total of at least 6% w/w of branched compounds of formula (I) with at least one of n and z<>0 and compounds of formula (II) with n<>0.

19. Polyalkylamines composition according to claim 1 comprising a total of at least 10% w/w of branched compounds of formula (I) with at least one of n and z<>0 and compounds of formula (II) with n<>0.

20. Polyalkylamines composition according to claim 1 comprising a total of at least 20% w/w of branched compounds of formula (I) with at least one of n and z<>0 and compounds of formula (II) with n<>0.

* * * * *